(12) United States Patent
Sacerio

(10) Patent No.: US 8,555,701 B1
(45) Date of Patent: Oct. 15, 2013

(54) ENHANCED METAL OXIDE GAS SENSOR

(75) Inventor: Jose L. Sacerio, Hialeah, FL (US)

(73) Assignee: CPS Products, Inc., Hialeah, FL (US)

( * ) Notice: Subject to any disclaimer, the term of this patent is extended or adjusted under 35 U.S.C. 154(b) by 312 days.

(21) Appl. No.: 13/198,816

(22) Filed: Aug. 5, 2011

(51) Int. Cl.
*G01N 27/12* (2006.01)

(52) U.S. Cl.
USPC ........................................ 73/31.06; 73/31.05

(58) Field of Classification Search
USPC ............................................. 73/31.05, 31.06
See application file for complete search history.

(56) References Cited

U.S. PATENT DOCUMENTS

| | | | |
|---|---|---|---|
| 4,580,439 A * | 4/1986 | Manaka | 73/31.06 |
| 4,938,928 A * | 7/1990 | Koda et al. | 422/98 |
| 4,980,557 A * | 12/1990 | Myers et al. | 250/423 R |
| 5,526,280 A | 6/1996 | Consadori et al. | |
| 6,644,098 B2 | 11/2003 | Cardinale et al. | |
| 7,350,396 B2 | 4/2008 | Huang et al. | |
| 7,631,537 B2 | 12/2009 | Tada et al. | |
| 7,820,949 B2 | 10/2010 | Sasaki et al. | |
| 2006/0228261 A1 * | 10/2006 | Iwamoto et al. | 422/88 |
| 2008/0038590 A1 * | 2/2008 | Nakakubo | 429/12 |
| 2008/0134753 A1 * | 6/2008 | Jun et al. | 73/23.2 |
| 2009/0100906 A1 * | 4/2009 | Bonne | 73/25.03 |
| 2009/0151429 A1 * | 6/2009 | Jun et al. | 73/31.06 |
| 2010/0089122 A1 | 4/2010 | Abdullah et al. | |
| 2010/0122568 A1 | 5/2010 | Inoue et al. | |
| 2011/0268148 A1 * | 11/2011 | King et al. | 374/31 |
| 2012/0297860 A1 * | 11/2012 | Izawa et al. | 73/31.05 |

FOREIGN PATENT DOCUMENTS

| | | |
|---|---|---|
| JP | 9043184 | 2/1997 |
| JP | 9138209 | 5/1997 |

* cited by examiner

*Primary Examiner* — David A Rogers
(74) *Attorney, Agent, or Firm* — Malin Haley DiMaggio & Bowen, P.A.

(57) ABSTRACT

A metal oxide sensor employing a method of heating that reduces the power required to heat the sensor to an optimal operating temperature and a method to automatically regulate and maintain the temperature of the sensors in the presence of air currents and other ambient conditions. The ultra miniature metal oxide sensors used have a thermal time constant short enough to allow for heating of the ultra miniature metal oxide sensors to occur with very narrow pulses of electricity. Such narrow pulses used to heat the sensor and to maintain the temperature such that the methods for reducing the power requirement apply throughout sensor's operation.

19 Claims, 3 Drawing Sheets

ENHANCED METAL OXIDE GAS SENSOR

CROSS REFERENCE TO RELATED APPLICATIONS

N/A

STATEMENT REGARDING FEDERALLY SPONSORED RESEARCH OR DEVELOPMENT

N/A

BACKGROUND OF THE INVENTION

1. Field of the Invention

The present invention relates to improvements in potentiating and operating metal oxide sensors for the detection of a variety of gases and vapors. In particular, the present invention relates to the use of metal oxide sensors having a lower operational power requirement and an automatic regulation of the sensor's surface temperature.

2. Description of the Related Art

The use of metal oxide sensors for the detection of a variety of gases and vapors is well known. These sensors are rugged, very sensitive and relatively inexpensive to manufacture. They respond to the presence of the target gas by changing the conductivity of the material over a large range of values which allows for the use of simple electronic circuits to produce a useful output. Some form of Tin Oxide is often used in this capacity.

At temperatures of several hundred degrees Celsius, the metal oxide material combines with the Oxygen molecules in the air to produce a layer of negatively charged ions adsorbed to the surface of the material. The conduction of electricity in the metal oxide depends on the conductivity characteristics across the grain boundaries which make up the structure of the material. The layer of negatively charged ions on the surface of the material impedes the flow of negative charges across the boundaries making the material a poor conductor in the presence of clean air.

In the presence of reducing gases, however, the negative ions on the surface of the sensor become neutralized to an extent which depends on the concentration of the gas. This lowers the potential barrier across the grain boundaries and consequently, the conductivity of the material increases in proportion to the concentration of the gas.

One common issue that arises with the use of metal oxide sensors in a mobile setting stems from the amount power required to bring the sensor to its operating temperature. Because the temperature of the metal oxide sensing material must be brought to a relatively high temperature in order to operate, a typical sensor requires a substantial amount of electrical power in order to properly operate. At the present time, it is common for a metal oxide sensing material to require close to 1 Watt of power to elevate the material at a suitable operating temperature. For portable gas detectors using metal oxide sensors, however, this much power consumption results in poor battery life. One way to reduce this power requirement would be to use a sensor with a mass small enough to have relatively short thermal time constant.

In recent months, the introduction of new manufacturing techniques has led to the introduction of ultra miniature metal oxide sensors which require very little power to bring the surface temperature to the required high level for optimum operation. The miniaturization has allowed for the development of alternate techniques and arrangements that would reduce the power required to operate metal oxide sensors.

The introduction of such ultra miniature metal oxide sensors has, however, exacerbated certain existing challenges pertaining to the operation of metal oxide sensors, To achieve maximum efficiency, the atmosphere to be sampled must be drawn over the surface of the metal oxide sensor. The temperature of the metal oxide sensor is affected by the air current created when the atmosphere is drawn over its surface, or when the probe containing the sensor is moved rapidly through the air. For example, in the most basic operation of a metal oxide sensor, the atmosphere being sampled is often drawn over the sensor, which is typically done with the aid of a pumping mechanism. The air current created as a result is not necessarily constant and its variations cause the sensor's temperature to fluctuate. Also, modern portable leak detector usage often times demand that the technician sweep the sampling probe of the instrument over the suspected area, thereby producing variable air currents over the sensor and changing its temperature. If such an occurrence caused a metal oxide sensor to be unable to maintain a suitable operating temperature, the accuracy of its measurements would be adversely affected. The use of ultra miniature metal oxide sensors exacerbates this problem because a sensor with a smaller mass would likely have even more difficulty maintaining its operating temperature while in use.

U.S. Pat. No. 7,820,949 discloses a temperature control method that protects a sensor from damage and eliminates interference from ambient conditions such as condensation. The methods disclosed do not seek to maintain the temperature of the sensor at an optimum operating point or to do so while minimizing the power consumed.

U.S. Pat. No. 7,631,537 discloses a gas sensing apparatus that measures the thermal conductivity of a gas in an atmosphere containing moisture. This apparatus alternatively switches power from a heating element to a reference resistor to allow for the measurement of the resistance of the heating element. When the thermal conductivity of the gas surrounding the heating element changes so does the temperature of the heating element and its resistance. Notably, the apparatus disclosed does not keep the temperature of the heating element constant to provide an optimum condition for the sensing element to react to the presence of the gas being detected.

U.S. Pat. No. 7,350,396 teaches a system and method for identify the various gases in a mixture by varying the temperature of a metal oxide sensor by sending pulses of varying voltage amplitude to the heater. The effect of this is to heat the sensing element over a wide range of temperatures and utilize the response of the sensing element at different temperatures.

U.S. Pat. No. 6,644,098 discloses a method, system and apparatus for sensing the presence of at least one predetermined gas. While this reference seeks to regulate the temperature of the heater, it does not teach doing so using simple switching means and in a power conserving way.

U.S. Pat. No. 5,526,280 teaches a system and method for using a gas detecting device that first burns off oxides formed during periods of inactivity and then to brings the sensing element to the normal operating temperature. The sensor disclosed, however, could supply inaccurate readings if placed in air currents such as those produced when the sensor is used in conjunction with a pump to draw a sample of the gas because no attempt is made to regulate the temperature of the heater during operating.

U.S. Patent Application 2010/0089122 discloses a gas sensor system that seeks to conserve power by operating the gas sensor heater at a reduced temperature until increasing levels of the gas to be sensed are detected. At that point, the heater temperature is increased to improve the sensitivity of the sensing element at the higher contamination levels. There is no teaching to keep the temperature of the heating element in a gas sensor constant and the temperature of the heater is not regulated since the heater is always powered by fixed amplitude pulses of fixed duration and no feed back mechanism is disclosed to control the temperature of the heater. Power is simply also conserved by operating the sensor for short periods of time followed by long periods of inactivity until the concentration of the contaminant is sensed to increase.

U.S. Patent Publication 2010/0122568 teaches a sensor system in which the temperature of a gas sensor is measured and it is used to determine the characteristics of the drive method applied to the gas sensor. The heater control is used to maintain the temperature of the gas sensor and its environment within a predetermined range.

JP9043184A and JP9138209A each teach gas sensing methods and apparatuses. While these publications disclose pulsing the drive voltage to the heater and the sensing element, neither deals with temperature reducing power requirements while regulating of the heater in a metal oxide sensor in the presence of air currents and other ambient conditions.

What is needed is a gas sensing method and apparatus that utilizes metal oxide sensors that require less power to bring their temperature to the high level required for optimum operation and while providing enhanced reliability by maintaining them at the optimum operating temperature by automatically regulating the temperature of the heater in the presence of air currents and other ambient conditions.

BRIEF SUMMARY OF THE INVENTION

The present invention relates to the potentiating and operation of metal oxide sensors for the purpose of detecting various gases and vapors. The sensing apparatus utilized in the present invention is an ultra miniature metal oxide sensor comprising metal oxide sensor material to detect gases and vapors in the air with a metal heater element embedded into the sensor material that can be used to heat up said sensor material. In the preferred embodiment, Tin Oxide is used for the sensor material and Platinum is used for the heater element.

The use of ultra miniature metal oxide sensors by itself could result in much lower electrical power requirement for raising the temperature of the sensors to an appropriate operating temperature. In this case, such miniaturization allows the implementation of the power reducing scheme of the present invention. To explain, the present invention said sensors are sized such that the thermal time constant of their mass is short enough to allow for heating of the ultra miniature metal oxide sensors to occur with very narrow pulses of electricity. Consequently, instead of requiring a constant voltage to be driven through the heater element, the temperature of the sensors can be raised by simply driving narrow pulses of a relatively high peak value through the heater element, which raises the temperature of the heater element and consequently the sensor material. Using narrow pulses of electricity, even pulses of a high peak value, serves to reduce the average current drawn from the power source. Thus, when the ultra miniature metal oxide sensors employed in the present invention are used in a portable gas detection device that utilizes battery power, battery life is much improved.

The present invention also employs an automatic temperature regulation method to ensure any variation in the temperature is automatically corrected and does not effect the accuracy of the ultra miniature metal oxide sensors' measurements. The Platinum wire used as the heater element has a positive temperature coefficient of resistance which can be used to determine the temperature of the sensor. This is done by using a high precision reference resistor with a fixed resistance equal to the resistance of the Platinum wire at a desired temperature. Thus, the temperature of the heating element, and thus the sensor, can be kept constant by applying voltage to the heater element and the reference until the heating element's resistance is equal to the resistance of the reference resistor. The resistance of the heater element and the reference resistor are subsequently compared periodically with additional voltage being applied whenever the heating element's resistance does not equal the resistance of the reference resistor.

This automatic temperature regulation method is also used to bring the ultra miniature metal oxide sensors to a higher temperature than the normal operating temperature in order to clean or rejuvenate the sensor material. When used to bring the sensors to a higher temperature, the method utilizes a reference resistor with a value equal to the value of the heater at the higher, cleaning temperature.

It is an objective of the present invention to provide a metal oxide sensor that requires less power to bring their temperature to the high level required for optimum operation.

It is another objective of the present invention to provide a method for bringing the temperature of a metal oxide sensor to the high level required for optimum operation with a reduced power requirement.

It is another objective of the present invention to provide a method for maintaining the temperature of a metal oxide sensor constant over a wide range of air current values.

It is another objective of the present invention to maintain the temperature of a metal oxide sensor constant while employing the method for bringing the temperature of a metal oxide sensor to the high level required for optimum operation with a reduced power requirement.

These and other objects and advantages of the present invention will become apparent through the drawings and the accompanying description set forth hereinafter.

DETAILED DESCRIPTION OF THE INVENTION

Figure 1:
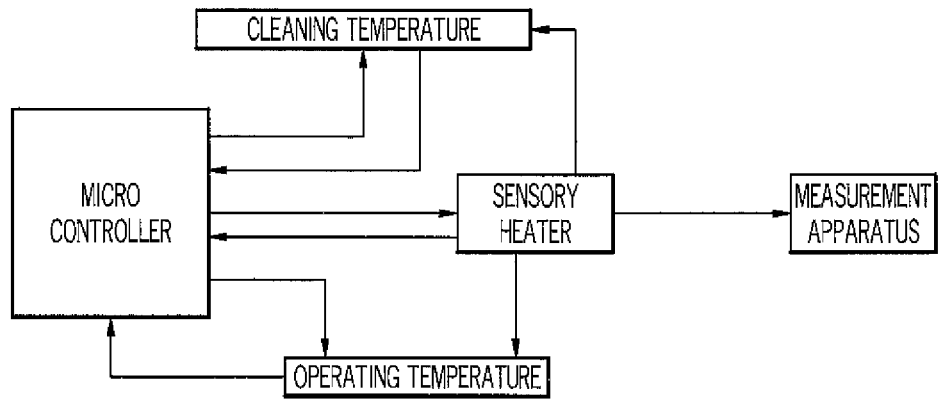
FIG. 1 is a block diagram of the interaction between the electronic components of a metal oxide sensor built in accordance with the present invention.

A metal oxide sensor system, built in accordance with the present invention, will now be described with initial reference to FIG. 1. The primary electrical components necessary to the functions of a sensor system built in accordance with the present invention are a microcontroller, a metal oxide sensor with an embedded heater, an operating temperature system, a cleaning temperature system, and a measurement preparation system. The microcontroller's electric connection with the metal oxide sensor, the operating temperature system, and the cleaning temperature system allows it apply electrical voltage to these components and utilize feedback mechanisms to optimize the operation of the sensor. In addition, electrical voltage which passes through the sensor is then routed to the measurement preparation system to allow the computation of the resistance value of the sensor material. This resistance value subsequently is used to determine the concentration of the impurity gas.

The sensor system is configured to be able to run in two distinct operating cycles. First, there is a normal operating cycle, which is the cycle in which the metal oxide sensor is heated to and maintained at an optimum temperature for accurate detection and measurement of the quantity of a variety of gases and vapors in its presence. This normal operating cycle requires application of electricity to the sensor, along with its embedded heater, and the operating temperature system as well as utilization of particular operating temperature feedback from the heater and the operating temperature system. Second there is a cleaning operating cycle, which is the cycle in which the metal oxide sensor is heated to a temperature high than that of the normal operating cycle for a short period of time, which functions to clean or rejuvenate the sensor material. This cleaning operating cycle requires application of electricity to the sensor, along with its embedded heater, and the cleaning temperature system as well as the utilization of cleaning temperature feedback from the heater and the cleaning temperature system.

In a preferred embodiment, the cleaning operating cycle is runs first in order to eliminate impurities which could interfere with sensor operation. The normal operating cycle runs second in order to obtain a measurement.

A suitable sensor utilizes a small metal coil embedded in its sensor material as its heater element. This heater element is Platinum in the preferred embodiment. Electrical voltage is applied to this heater to raise its temperature, which in turn raises the temperature of the sensor material in which the heater is embedded. Platinum is chosen because of its high melting temperature and its chemical inertness. In this embodiment, a form of Tin Oxide is used as sensor material.

Electrical voltage is applied to the heater element by the microprocessor. The voltage applied to the heater to raise its temperature can be a constant voltage or a function of time. The sensor heating mode of the present embodiment, however, utilizes voltage applied as a function of time in order to reduce the average current drawn from the power source to operate the sensor and allow for the integration of a method that provides for the automatic regulation of the sensor's temperature.

The reduction in average current drawn resulting from the use of the method of the present invention is illustrated as follows. The voltage required to heat up a filament heater to a given temperature is expressed in terms of its root mean square ("RMS") value. With constant, direct current voltage, the power delivered to a heater of resistance R is:

$$\text{Power delivered} = V(dc)^2/R. \tag{I}$$

But if the voltage varies with time, then the RMS value of the voltage waveform is used to compute the power that the time varying waveform delivers to the heater of resistance R:

$$\text{Power delivered} = V(rms)^2/R. \tag{II}$$

In other words, the RMS value of a time varying voltage waveform equals the value of the constant voltage which would deliver the same power to the heater in question.

The average current drawn for the source of voltage, however, is not the same. If V(rms) is required to heat up a heater of resistance R to a given temperature, and a direct current voltage of V(rms) is used, the average current would be:

$$I(avg) = V(rms)/R. \tag{III}$$

But if a train of pulses of peak value V(p), on-time T(on), and period T is used, the RMS value of that pulse train is:

$$V(prms) = V(p) * \text{SQRT}(T(on)/T). \tag{IV}$$

Since V(prms) needs to be equal in value to V(ims) to deliver the same power to the heater, V(p) needs to be:

$$Vp = Vrms/\text{SQRT}(T(on)/T). \tag{V}$$

It is evident that a pulse train of peak value V(rms)/SQRT (Ton/T), on-time T(on) and period T will deliver the same power to a heater of resistance R as a constant voltage of value Vrms. However, the average current drawn from the source of the pulses will be:

$$I(pavg) = \{Vrms/\text{SQRT}(T(on)/T)\} * (T(on)/T)/R. \tag{VI}$$

Compared with I(avg) from equation III, it follows that:

$$I(pavg) = I(avg) * (T(on)/T)/\text{SQRT}(T(on)/T). \tag{VII}$$

Thus, by using a train of pulses the current consumption has been decreased by the ratio of the duty cycle of the pulse train (T(on)/T) to the square root of the duty cycle.

For example, in the preferred embodiment, a sensor requires 0.8 V RMS to heat up to the working temperature. The heater's resistance is 7 OHMS at that temperature. If a regulated 0.8 V direct current source is used to power the heater, the current drawn will be:

$$I(avg) = 0.8/7 = 114 \text{ mA}. \tag{VIII}$$

A train of 5 volt pulses with an on-time of 25.6 microseconds and a period of 1.0 millisecond, the RMS voltage obtained is:

$$V(prms) = 5 * \text{SQRT}(0.0256) = 0.8 \text{ V RMS}. \tag{IX}$$

The average current, however, is:

$$I(pavg) = (5/7) * (0.0256) = 18.3 \text{ mA}. \tag{X}$$

Consequently, the use of a train of pulses in the present invention leads to a reduction in average current drawn by over 80 percent.

It must be noted, however, that the use of such a train of pulses is made practical and effective by the recent introduction of new manufacturing techniques which have allowed manufacturers to introduce ultra miniature metal oxide sensors which require very little time to bring the surface temperature to the required high level for optimum operation. These miniaturized sensors, as used in the present invention, allows the implementation of the power reducing scheme the thermal time constant of the mass being heated is short enough to allow for heating to occur with very narrow pulses.

The use of these miniature sensors does create an added hurdle which must be addressed. A metal oxide sensor with a mass small enough to benefit from the pulsed drive method outlined above is also very likely to have its surface temperature affected by environmental conditions, especially air currents. In all sensing applications using such sensors, the atmosphere being sampled for gas or vapor contaminants must be drawn over the sensor. This is done with the aid of a pumping mechanism. This air current is not necessarily constant and its variations cause the sensor's temperature to fluctuate. Also, modem portable leak detector usage demands that the technician sweep the sampling probe of the instrument over the suspected area, thereby producing variable air currents over the sensor and changing its temperature.

Consequently, the present invention's utilizes a sensor heating mode that provides a method to maintain the temperature of the sensor constant over a wide range of air current values while still maintaining the current saving pulsed drive method outlined above. This is done by utilizing the positive temperature coefficient of resistance found in the Platinum heater wire used for the heater in the sensor is used to determine the temperature of the sensor's mass.

In one embodiment, every 5.8 milliseconds (170 Hz.), microprocessor 10 applies 5 volts to the heater 11b through a fixed resistor 20 and to resistor strings 21, 22, and 23, 24, 25. Voltage is applied to the heater until voltage comparators 12 and 13 sense that the heater resistance has reached the desired value, at which point the 5 volts applied to the heater is removed.

Comparator 13 is used in the cleaning cycle and it compares the resistance of the heater 11b to the value of resistors 24 and 25 combined. Comparator 12 is used in the normal operating cycle and compares the resistance of heater 11b to the value of resistor 22.

In this manner, the heater is brought to the desired temperature in the face of varying conditions such as fluctuations in the air current over the sensor.

For example, if the air current over the heater is strong, more power is needed to reach the desired operating temperature since the air current caries some of the heat energy away. In this case, the microcontroller keeps the 5 volts on for a longer period of time since it takes longer for the heater to reach the value of the reference resistor.

The measurement of sensor resistance is made immediately after the power to the heater is removed so the heater voltage does not interfere with the measurement.

One skilled in the art will recognize that many different operating temperatures may be obtained with this method simply by multiplying the number of comparators and comparison resistor strings.

Figure 2:
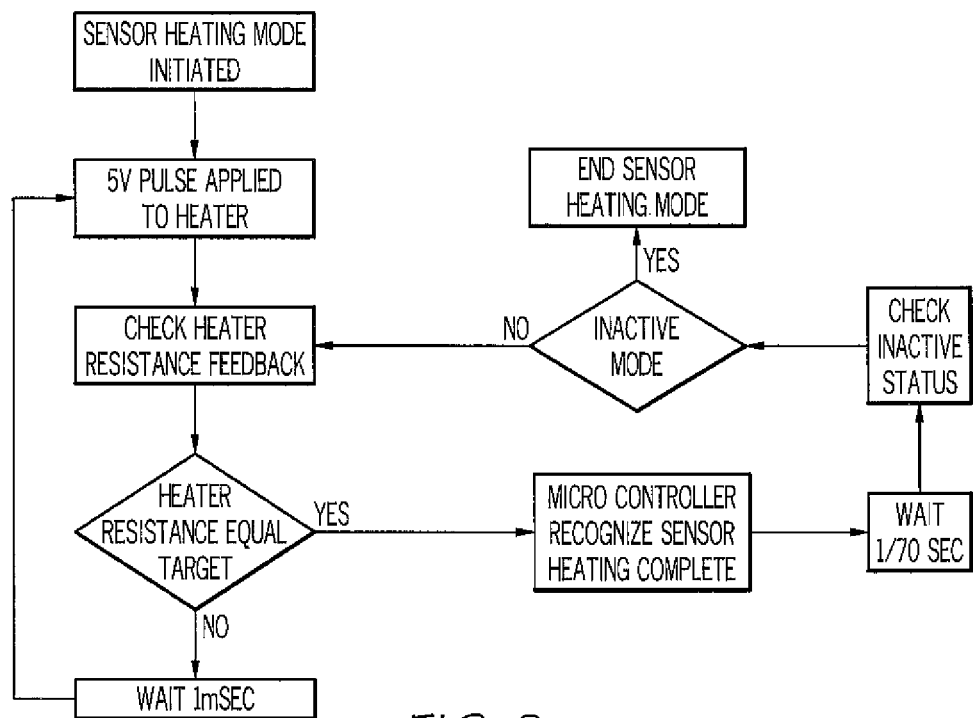
FIG. 2 is a flow chart showing the method of heating the metal oxide sensor to a desired temperature level in accordance with the present invention.

To illustrate with reference to FIG. 2, when the sensor heating mode is initiated, voltage is applied to the sensor's heater by the microprocessor. This voltage is applied as a function of time, with 5 Volts of electricity being applied to the heater for 25.6 microseconds. This voltage pulse will be applied every 1 millisecond provided the feedback indicates that heater's temperature needs to be raised. This voltage is also applied concurrently to the operating temperature system and the cleaning temperature system. If the normal operating cycle is active, the microprocessor checks the heater resistance feedback in the form of the operating temperature feedback provided by the operating temperature system to determine whether the heater's temperature needs to be raised. The operating temperature system utilizes a fixed, high precision resistor of a resistance value equal to the value of the heater's resistance at the desired temperature. The operating temperature system compares the resistance value of the heater and provides one of two distinct operating temperature feedbacks to the microprocessor. The first operating temperature feedback is the heater's resistance is lower than that of the reference resistor, which indicates to the microprocessor to apply a voltage pulse to the heater. The second operating temperature feedback is the heater's resistance is equal to or greater than that of the reference resistor, which indicates to the microprocessor to cease the application of voltage to the heater. Thus, when the resistance of the heater equals the resistance of the reference resistor, the microprocessor is notified that the heating is complete and the application of voltage to the heater ceases.

This temperature regulating method is also used to select a higher temperature than the optimum operating value for a short period of time. This elevated temperature is used to clean or rejuvenate the sensor material. When the cleaning operating cycle is active, the microprocessor checks the heater resistance feedback in the form of the cleaning temperature feedback provided by the cleaning temperature system to determine whether the heater's temperature needs to be raised. The cleaning temperature system utilizes its own fixed, high precision resistor of a resistance value equal to the value of the heater's resistance at the desired temperature for cleaning. The cleaning temperature system compares the resistance value of the heater and provides one of two distinct operating temperature feedbacks to the microprocessor. The first cleaning temperature feedback is the heater's resistance is lower than that of the reference resistor, which indicates to the microprocessor to apply a voltage pulse to the heater. The second cleaning temperature feedback is the heater's resistance is equal to or greater than that of the reference resistor, which indicates to the microprocessor to cease the application of voltage to the heater. Thus, when the resistance of the heater equals the resistance of the reference resistor, the microprocessor is notified that the heating is complete and the application of voltage to the heater ceases.

As long as the sensor system has either the normal operating cycle or the cleaning operating cycle active, it will repeat its heating method at a fixed frequency. Once being notified to cease to application of voltage to the heater, at a constant rate of 170 Hz, the microprocessor will check the active status of the sensor system. As soon as the heater voltage is turned off, the resistance of the metal oxide semiconductor sensor is measured to determine the presence of a contaminating gas and its concentration. This cycle is repeated at a fixed frequency. In essence, the duty cycle of this pulsed drive is modulated to precisely generate the power needed to heat the sensor to the optimum temperature in the face of varying wind conditions and ambient temperature fluctuations. If the normal operating cycle or the cleaning operating cycle is active, the microprocessor will again check the feedback from the feedback of the active cycle and use it to make the above determination of whether to apply a voltage pulse to the heater. If neither the normal operating cycle nor the cleaning operating cycle is active, the microprocessor will exit the sensor heating mode.

Figure 3:
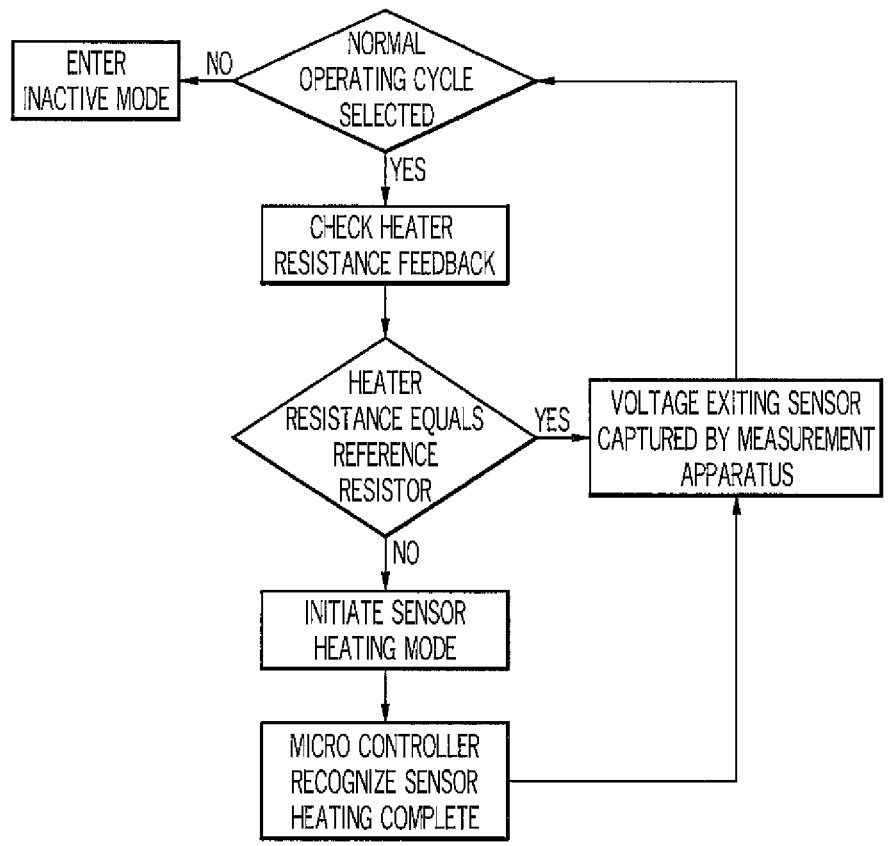
FIG. 3 is a flow chart showing the method of operating for the normal operating cycle for sensing and measure the concentration of gas in accordance with the present invention.

Referring now to FIG. 3, the normal operating cycle is one of the two operating cycles of the present invention. When the normal operating cycle is selected, the microprocessor begins by referencing the operating temperature feedback to confirm the heater's resistance is lower than that of the reference resistor in the operating temperature system. If the heater's resistance is not lower than that of the reference resistor, the measuring apparatus immediately captures the voltage exiting the sensor for use in calculating the presence and concentration of gas. The microprocessor then begins the process again by determining if the normal operating cycle is still selected.

If the heater's resistance is lower than that of the reference resistor, the microprocessor initiates the sensor heating mode and sets the target resistance for the heater to be the reference resistor of the operating temperature system. The sensor heating mode remains initiated until the microprocessor receives operating temperature feedback indicating the heater's resistance is not lower than that of the reference resistor. Consequently, once this feedback is recognized, the measuring apparatus immediately captures the voltage exiting the sensor for use in calculating the presence and concentration of gas. Taking a reading right after the temperature is reached, allows for maximum accuracy and stability of the results while maintaining a fast response to changing concentrations of the impurity gas or vapor.

Figure 4:
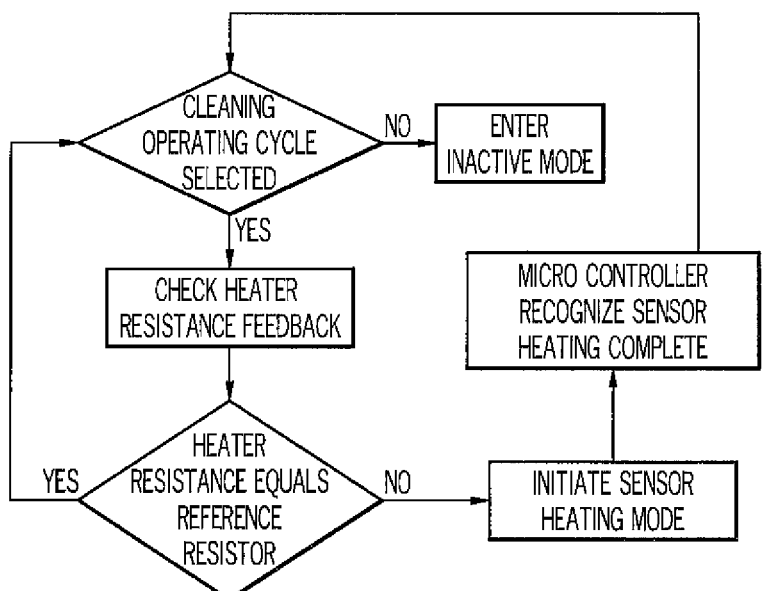
FIG. 4 is a flow chart showing the method of operating for the cleaning operating cycle for cleaning and rejuvenating the sensor material in accordance with the present invention.

Referring now to FIG. 4, the cleaning operating cycle is the other of the two operating cycles of the present invention. When the cleaning operating cycle is selected, the microprocessor begins by referencing the cleaning temperature feedback to confirm the heater's resistance is lower than that of the reference resistor in the cleaning temperature system. If the heater's resistance is not lower than that of the reference resistor, the microprocessor terminates the cycle and checks the active mode status to determine if the cleaning operating cycle is still selected.

If the heater's resistance is lower than that of the reference resistor, the microprocessor initiates the sensor heating mode and sets the target resistance for the heater to be the reference resistor of the cleaning temperature system. The sensor heating mode remains initiated until the microprocessor receives cleaning temperature feedback indicating the heater's resistance is not lower than that of the reference resistor. Consequently, once this feedback is recognized, the heater has reached a suitable temperature for the sensor material to be cleaner and rejuvenated.

Figure 5:
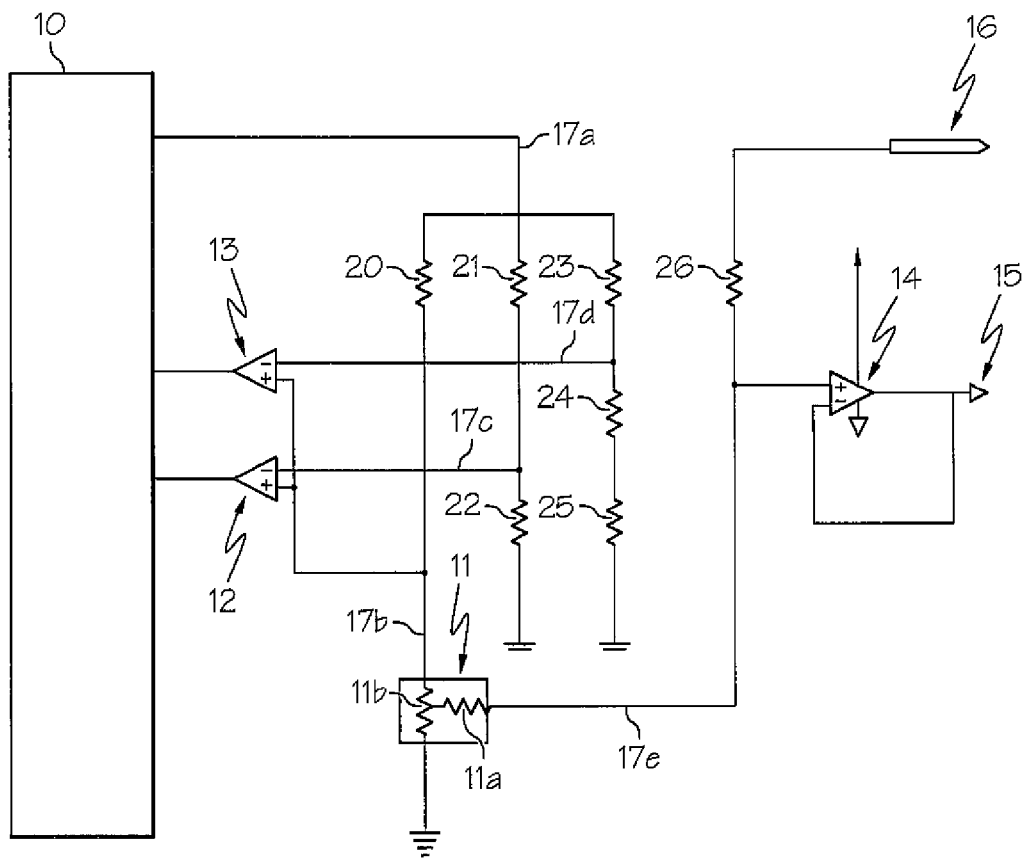
FIG. 5 is a schematic diagram of the electrical wiring of a metal oxide sensor built in accordance with the present invention.

Referring now to FIG. 5, the operating temperature system and the cleaning temperature system each begin with the microcontroller 10 applying voltage between point 17a and ground, sending current through an operating resistor 20 and the sensor's heater 11b, as well as a first reference resistor 21, second reference resistor 22, a third reference resistor 23, a fourth reference resistor 24, and a fifth reference resistor 25. The heater 11b, which has a variable resistance that is a function of its temperature, has a low resistance initially because the heater is at room temperature. This keeps the output of operating temperature system comparator 12 and the cleaning temperature system comparator 13 low since their negative inputs are at a higher voltage. The operating temperature comparator 12 and its connected wiring and resistors comprise the operating temperature system. The cleaning temperature comparator 13 and its connected wiring and resistors comprise the cleaning temperature system. As the heater temperature rises, the voltage at point 17b increases and it will reach the voltage at point 17c when its temperature reaches the desired operating temperature value and the voltage at point 17d when the temperature reaches the desired cleaning temperature value.

When the voltage at point 17b reaches the voltage at point 17c, the output pin of the operating temperature system comparator 12 will switch to high. When the voltage at point 17b reaches the voltage at point 17d, the output pin of the cleaning temperature system comparator 13 will switch to high. These serve as the operating temperature feedback and cleaning temperature feedback loops which send to the microcontroller information on the temperature of the sensor.

The cleaning operating cycle is implemented by programming the microcontroller to apply a voltage to point 17a and turn it off when the cleaning temperature system comparator's 13 output switches high. This is repeated at a constant rate of 170 Hz and heats the sensor to higher temperature than the one maintained in normal operation because the voltage at point 17d is higher than the voltage at point 17e.

The normal operating cycle is implemented by programming the microcontroller to apply a voltage at point 17a and turn it off when the operating temperature system comparator's 12 output switches high. This is also repeated at a constant rate of 170 Hz. The optimum operating temperature of the sensor, which by the nature of the metal oxide material it is composed of has a variable resistance that depends on the particular gases or vapors present, is reached when the operating temperature system's comparator's 12 output switches high. In this mode of operation, the voltage at point 17e is buffered by the measurement preparation system amplifier 14 and sent to a measure system 15. The measurement preparation system amplifier 14, measurement preparation resistor 26, and measurement preparation reference voltage 16 comprise the measurement preparation system. The measurement preparation resistor 26 and measurement preparation reference voltage 16 provide reference parameters which allow the computation of the resistance value of the sensor material based on the voltage at point 17e. This resistance is inversely proportional to the concentration of the impurity gas.

Figure 6:
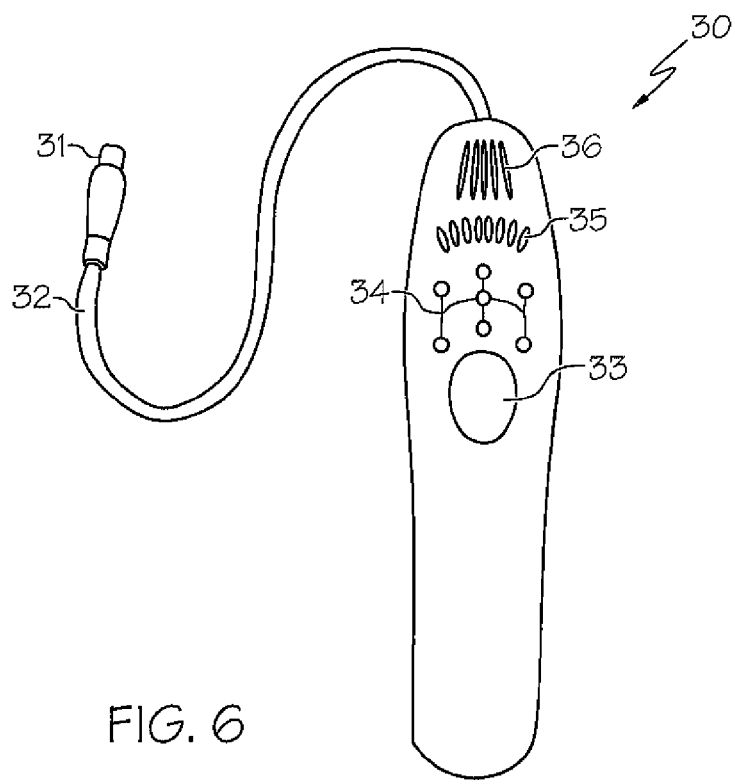
FIG. 6 is a front elevation view of the device containing a metal oxide sensor built in accordance with the present invention.

Referring now to FIG. 6, a sensing device 30 housing a sensor system built in accordance with the present invention is defined by an elongated body sized to be held in its users hand with a flexible probing cord 32 that can access narrow spaces or other hard to reach areas. At the end of the probing cord 32 opposing where it is attached to the elongated body is the sensor apparatus 31, which houses the metal oxide sensor. The housing has one manual interface 33 which is used to activate it and initiate operating cycles. The sensing device allows for a plurality of sensitivity settings, where a higher sensitivity setting is desirable for small leaks and a lower sensitivity setting is desirable for larger leaks. Because such metal oxide sensors can be sensitive to leaks a small as thirty-five (35) parts per million, the ability to adjust the sensitivity setting is desirable so that the sensor can provide accurate its results using an appropriate perspective. As this embodiment of the sensing device 30 automatically adjusts sensitivity, sensitivity level indicators 34 are included allow for a visual indication to the user the selected sensitivity level.

Another visual feedback provided to the user is provided by a plurality of LEDs are used to create a tachometer style bar graph display 35. This graph display 35 provides a visual indication of the leak size and allows its user to quickly pinpoint the exact location of the leak. A speaker 36 is included to provide an audible notification in the form of a loud, variable frequency audible alarm indication of the leak.

The present invention is not limited to the specific embodiments described. Many different embodiments exist without departing significantly from the scope or the spirit of the present invention. The described embodiments thus serve as examples of the present invention and are not restrictive of the scope of the invention.

What is claimed is:

1. A method of operating a semiconductor gas sensor comprising the steps of:
  providing a controller connected to a power supply, said controller being capable of applying electricity, ceasing the application of electricity, and receiving electrical signals through electrical connections;
  providing a sensing apparatus having a heating element and a sensing element, where the sensing apparatus is electrically connected to said controller through a first electrical pathway, the heating element increases in temperature when electricity is applied, the resistance of said heating element increases when the temperature of said heating element increases, the temperature of said sensing element increases when the temperature of said heating element increases, and the sensing element is a semi conductive material with a conductivity that changes in response to changes in its temperature;
  providing an operating temperature system comprising an operating comparator and an operating resistor of fixed resistance, said operating comparator having distinct electrical connections to said controller and said sensing apparatus and being able to compare the resistance of the operating resistor and the heating element, said operating comparator being able to provide an operating temperature signal electronically to the controller when the resistance of the heating element is not less than the resistance of the operating resistor; and where the controller applies electricity through the heating element in a series of narrow pulses.

2. The method of claim 1, additionally comprising the steps of:

causing the controller to apply electricity through the heating element until said controller receives said operating temperature signal; and causing the controller to apply electricity through the sensing element upon receiving said operating temperature signal.

3. The method of claim 1, where said operating temperature signal is provided continuously to said controller as long as the resistance of the heating element is less than the resistance of the operating resistor; and said controller applies electricity through the heating element as long as said controller is not receiving said operating temperature signal.

4. The method of claim 1, additionally comprising the steps of:

providing a cleaning temperature system comprising a cleaning comparator and a cleaning resistor of fixed resistance, said cleaning comparator having distinct electrical connections to said controller and said sensing apparatus and being able to compare the resistance of the cleaning resistor and the heating element, said cleaning comparator being able to provide an cleaning temperature signal electronically to the controller when the resistance of the heating element is equal to the resistance of the cleaning resistor; and causing the controller to apply electricity through the heating element until said controller receives said operating temperature signal.

5. The method of claim 1, additionally comprising the step of providing a measurement preparation system electrically connected to said controller through said sensor element, where electricity applied through the sensing element by said controller is routed to said measurement preparation system.

6. The method of claim 5, where said measurement preparation system comprises a measuring amplifier and a measuring resistor in parallel electrical connections, said measuring comparator being wired to buffer the electricity routed to said measurement preparation system.

7. A semiconductor gas sensor comprising:

a controller connected to a power supply, said controller being capable of applying electricity, ceasing the application of electricity, and receiving electrical signals through electrical connections;

a sensing apparatus having a heating element and a sensing element, where the sensing apparatus is electrically connected to said controller through a first electrical pathway, the heating element increases in temperature when electricity is applied, the resistance of said heating element increases when the temperature of said heating element increases, the temperature of said sensing element increases when the temperature of said heating element increases, and the sensing element is a semi conductive material with a conductivity that changes in response to changes in its temperature;

an operating temperature system comprising an operating comparator and an operating resistor of fixed resistance, said operating comparator having distinct electrical connections to said controller and said sensing apparatus and being able to compare the resistance of the operating resistor and the heating element, said operating comparator providing an operating temperature signal electronically to the controller when the resistance of the heating element is not less than the resistance of the operating resistor; and where when electricity has been applied through the heating element until the said controller receives said operating temperature signal, the controller applies electricity through the sensing element.

8. The sensor of claim 7, where the controller applies electricity through the heating element in a series of narrow pulses.

9. The sensor of claim 7, where said operating temperature signal is provided continuously to said controller as long as when the resistance of the heating element is not less than the resistance of the operating resistor; and said controller applies electricity through the heating element as long as said controller is not receiving said operating temperature signal.

10. The sensor of claim 7, additionally comprising a cleaning temperature system comprising a cleaning comparator and a cleaning resistor of fixed resistance, said cleaning comparator having distinct electrical connections to said controller and said sensing apparatus and being able to compare the resistance of the cleaning resistor and the heating element, said cleaning comparator being able to provide an cleaning temperature signal electronically to the controller when the resistance of the heating element is equal to the resistance of the cleaning resistor.

11. The sensor of claim 7, additionally comprising a measurement preparation system electrically connected to said controller through said sensor element, where electricity applied through the sensing element by said controller is routed to said measurement preparation system.

12. The sensor of claim 11, where said measurement preparation system comprises a measuring amplifier and a measuring resistor in parallel electrical connections, said measuring comparator being wired to buffer the electricity routed to said measurement preparation system.

13. A method of operating a semiconductor gas sensor comprising the steps of:

providing a controller means for applying electricity, ceasing the application of electricity, and receiving electrical signals through electrical connections;

providing a sensing means providing first variable resistance in a circuit the presence of gas or vapor;

providing a heating means for heating said sensing means and providing a second variable resistance in a circuit due to changing temperature;

providing an operating temperature system means for comparing the second variable resistance to a operating fixed resistance and for providing an operating signal to the controller when the second variable resistance is not less than the operating fixed resistance; and where the controller means applies electricity through the heating means in a series of narrow pulses.

14. The method of claim 13, additionally comprising the steps of:

causing the controller means to apply electricity through the heating means until said controller means receives said operating signal; and causing the controller means to apply electricity through the sensing means upon receiving said operating signal.

15. The method of claim 13, where
said operating signal is provided continuously to said controller means as long as the resistance of the heating means is not less than the fixed operating resistance; and
said controller means applies electricity through the heating mean as long as said controller means is not receiving said operating signal.

16. The method of claim 13, additionally comprising the steps of:
providing an cleaning temperature system means for comparing a third variable resistance to a cleaning fixed resistance and for providing a cleaning signal to the controller when the third variable resistance is not less than the cleaning fixed resistance; and
causing the controller to apply electricity through the heating element until said controller receives said cleaning signal.

17. The method of claim 13, where the heating means is embedded in the sensing means.

18. The method of claim 13, additionally comprising the step of providing a measurement preparation means for routing electricity applied through the sensing means.

19. The method of claim 18, where said measurement preparation means splits the electricity routed to said measurement preparation means into a first pathway and a second pathway and buffers the electricity in the first pathway.

* * * * *